United States Patent [19]
LePage, Jr. et al.

[11] Patent Number: 5,893,618
[45] Date of Patent: Apr. 13, 1999

[54] STACKING STERILIZING TRAY SYSTEM

[75] Inventors: Albert A. LePage, Jr., Weare; Heather P. Horton, Manchester, both of N.H.

[73] Assignee: Poly VAC, Inc., Manchester, N.H.

[21] Appl. No.: 08/897,458

[22] Filed: Jul. 21, 1997

[51] Int. Cl.$^6$ ................................................. A47B 47/00
[52] U.S. Cl. ................ 312/265.6; 312/213; 312/350; 312/209; 312/334.23
[58] Field of Search ........................... 312/265.6, 107, 312/108, 109, 126, 215, 244, 257.1, 270.3, 308, 311, 350, 351, 330.1, 334.23, 107.5, 209, 210, 210.5, 229, 293.1, 293.3, 223.1, 223.2, 213

[56] References Cited

U.S. PATENT DOCUMENTS

| | | | |
|---|---|---|---|
| 1,195,309 | 8/1916 | White | 312/333 X |
| 3,203,744 | 8/1965 | Batke et al. | 312/108 X |
| 3,691,634 | 9/1972 | Buchtel et al. | 32/22 |
| 3,752,547 | 8/1973 | Propst et al. | 312/108 X |
| 3,918,781 | 11/1975 | Paris | 312/111 |
| 4,118,086 | 10/1978 | Kneier | 312/311 |
| 4,140,355 | 2/1979 | Swain | 312/336.23 X |
| 4,389,078 | 6/1983 | Streit | 312/107 X |
| 4,509,805 | 4/1985 | Welsch et al. | 312/210 |
| 4,681,378 | 7/1987 | Hellman, III | 312/107 X |
| 4,753,495 | 6/1988 | Swink | 312/213 X |
| 5,048,902 | 9/1991 | Daly | 312/257.1 X |
| 5,069,466 | 12/1991 | Propst | 312/350 X |
| 5,069,511 | 12/1991 | Swets et al. | 312/107.5 |
| 5,211,915 | 5/1993 | Monch | 422/102 |
| 5,244,272 | 9/1993 | Thompson | 312/334.23 |
| 5,350,304 | 9/1994 | Fula et al. | 312/213 X |
| 5,423,605 | 6/1995 | Liv | 312/265.6 |
| 5,451,380 | 9/1995 | Zinnanti | 422/300 |
| 5,472,270 | 12/1995 | Czarnecky et al. | 312/265.6 |
| 5,588,728 | 12/1996 | Eldridge et al. | 312/223.1 X |
| 5,673,984 | 10/1997 | Insalaco et al. | 312/108 X |
| 5,718,491 | 2/1998 | Li | 312/107 |

*Primary Examiner*—Peter R. Brown
*Assistant Examiner*—James O. Hansen
*Attorney, Agent, or Firm*—Hayes, Soloway, Hennessey, Grossman & Hage, P.C.

[57] ABSTRACT

A sterilization, transporting and storage container tray assembly for a surgical instrument kit comprises a plurality of trays for accommodating surgical instruments, and a rack for holding the trays in a stacked arrangement. The trays are slidably, removably mounted in the rack, and are accessible from the side of the rack. A removable cap is provided for locking the trays in position in the rack, i.e. for transportation, sterilization and storage.

18 Claims, 8 Drawing Sheets

5,893,618

STACKING STERILIZING TRAY SYSTEM

BACKGROUND OF THE INVENTION

1. Field of the Invention

The present invention relates to sterilizing trays for surgical instruments, and, more particularly, to an improved storage and sterilization tray system for delivering a plurality of stacked trays for convenient access.

2. Brief Description of Related Prior Art

Surgical procedures are regularly performed using "sets" of pre-selected surgical instruments, each set being a collection of instruments established from experience to be useful in a given surgical procedure. For example, the surgical instruments expected to be used in an obstetrical procedure are grouped together to form a set, and, as a set, are sterilized, stored on a pan or tray, and finally transported on that pan or tray to the operating room when their use is required. Complex procedures typically involve a substantial number of instruments which generally are employed in a preset sequence. Thus, typically, several instrument trays may be necessary to accommodate all of the required surgical instruments. Accordingly, sterilizing cases often are designed to accommodate a plurality of stacking trays with the instruments arranged on the trays in such a manner that the trays are accessed one at a time as the surgical procedure advances. For example, as shown in FIG. 1, a sterilizing case 10 includes a bottom tray 12, one or more middle trays 14, a top tray 15 and a removable top or lid 16. Latch means 17 is provided for clamping the lid 16 to the base 12. Typically, latch means 20 may also include handles 9 for carrying the tray assembly 10.

While stacking tray sterilization cases such as shown in FIG. 1 have become widely adopted, such trays have certain disadvantages. For example, incorrect stacking of the trays, i.e. stacking the trays in the wrong order could be disruptive to operating room personnel while they hunt for the correct tray. Also, in extreme circumstances, precious time lost could compromise the safety of a patient. Also, it sometimes may be necessary for operating room personnel to access certain instruments out of normal order. If those instruments are buried in a lower positioned tray, precious time again may be lost.

SUMMARY OF THE INVENTION

Accordingly, it is a primary object of the present invention to overcome the aforesaid problems and disadvantages of the prior art. Another object of the invention is to provide a sterilization tray stacking system characterized by enhanced flexibility as compared to prior art stacking systems, and which provides ready access to any selected tray or trays in the stack.

The present invention provides a sterilization, transporting and storage container tray assembly for a surgical instrument kit, which comprise a plurality of trays for accommodating surgical instruments, and a rack for holding the trays in a stacked arrangement. The trays are slidably, removably mounted in the rack, and are accessible from the side of the rack. Means is provided for locking the trays in position in the rack, i.e. for transportation, sterilization and storage.

Other features, objects and advantages of the present invention will become apparent from the following description of a preferred embodiment of the invention taken in conjunction with the accompanying drawings, wherein like numerals denote like parts, and wherein:

DETAILED DESCRIPTION OF PREFERRED EMBODIMENTS

Figure 1:
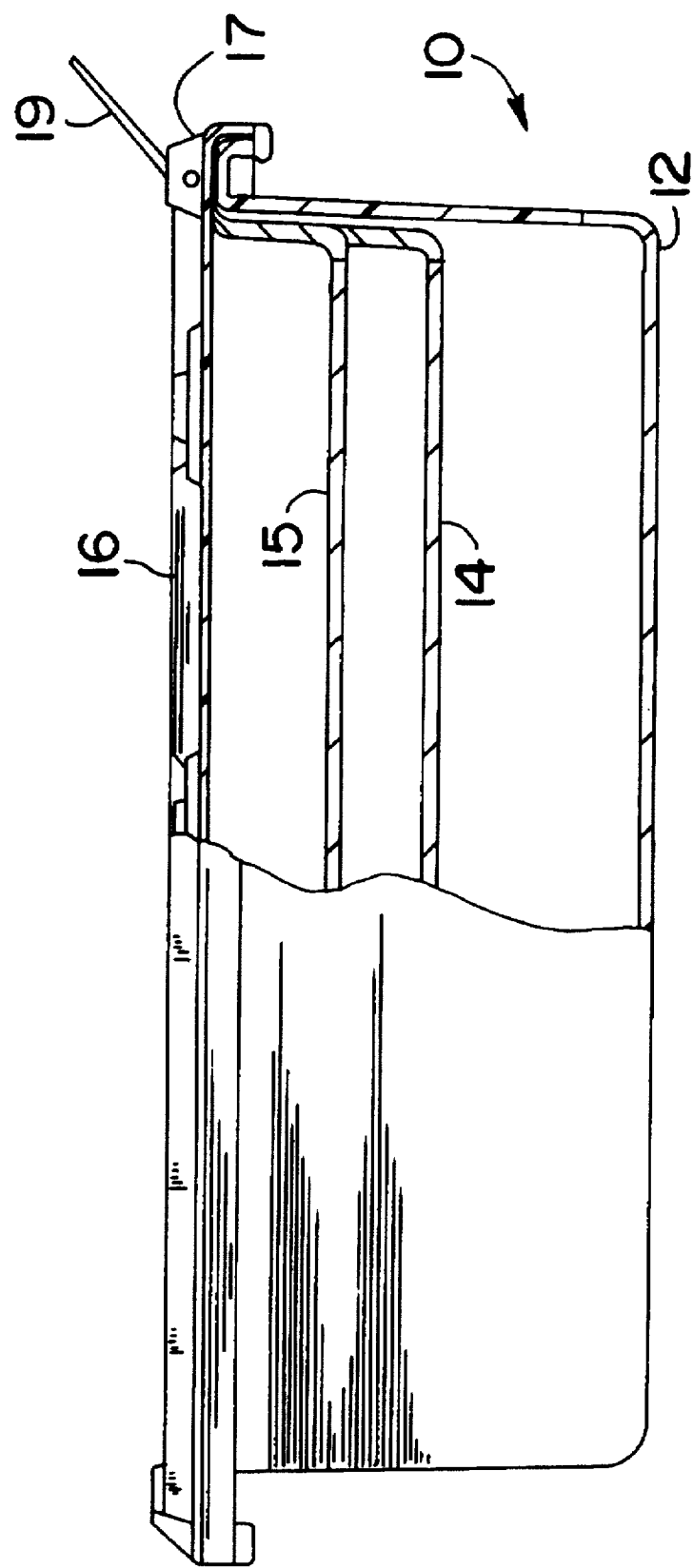
FIG. 1 is a side elevation view, in partial cross-section, of a stacking, multi-tray sterilization, transporting and storage container tray and rack system in accordance with the prior art.
Figure 2:
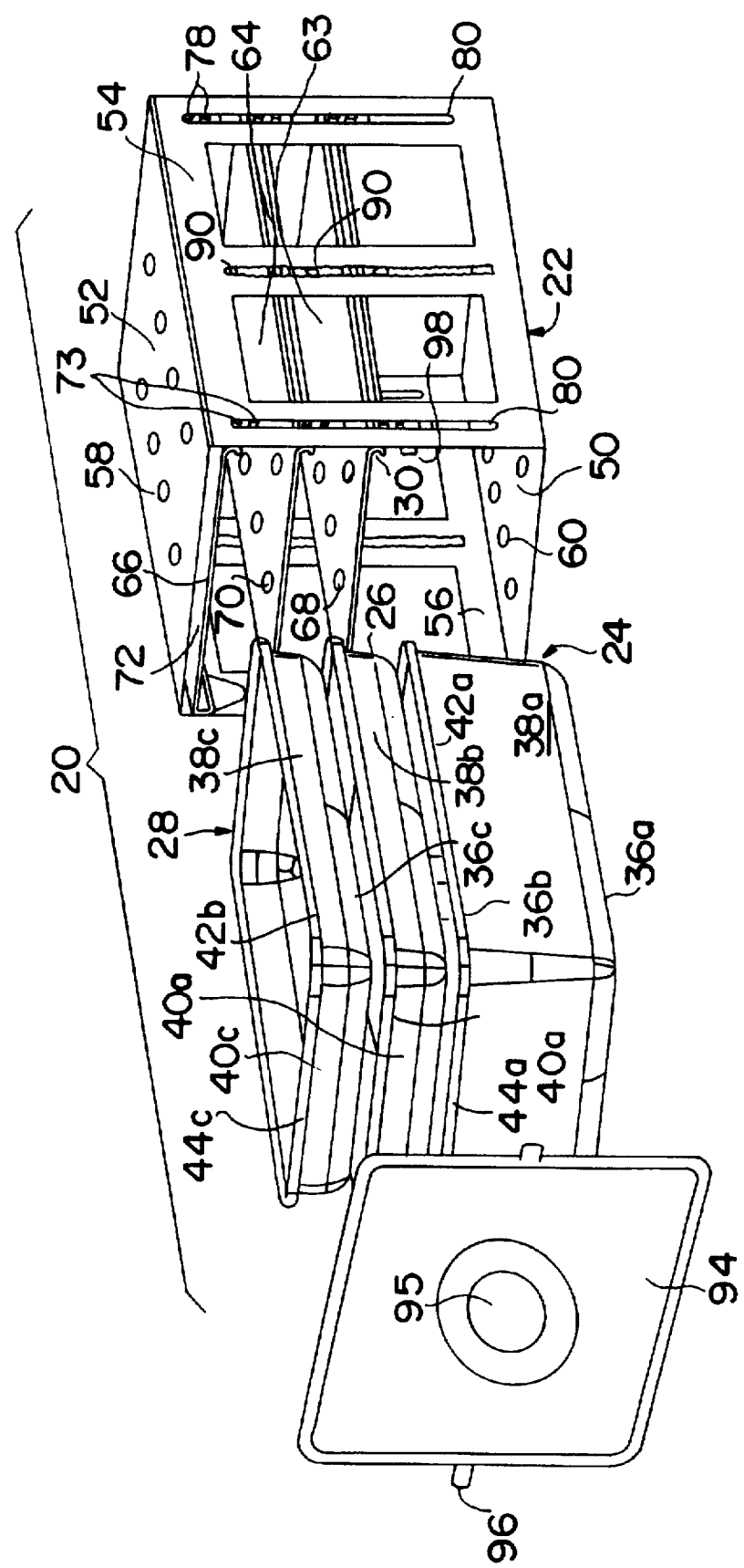
FIG. 2 is an exploded, perspective view of a stacking, multi-tray sterilization, transporting and storage container tray and rack system made in accordance with the present invention.
Figure 3:
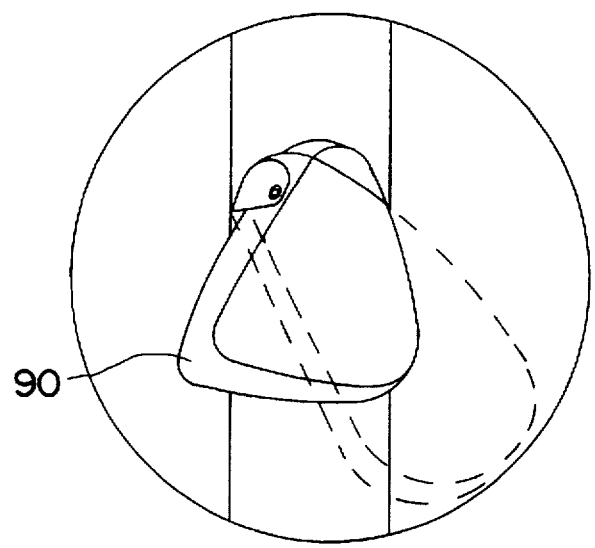
FIG. 3 is an enlarged view of the portion designed "FIG. 3" in FIG. 2.
Figure 4:
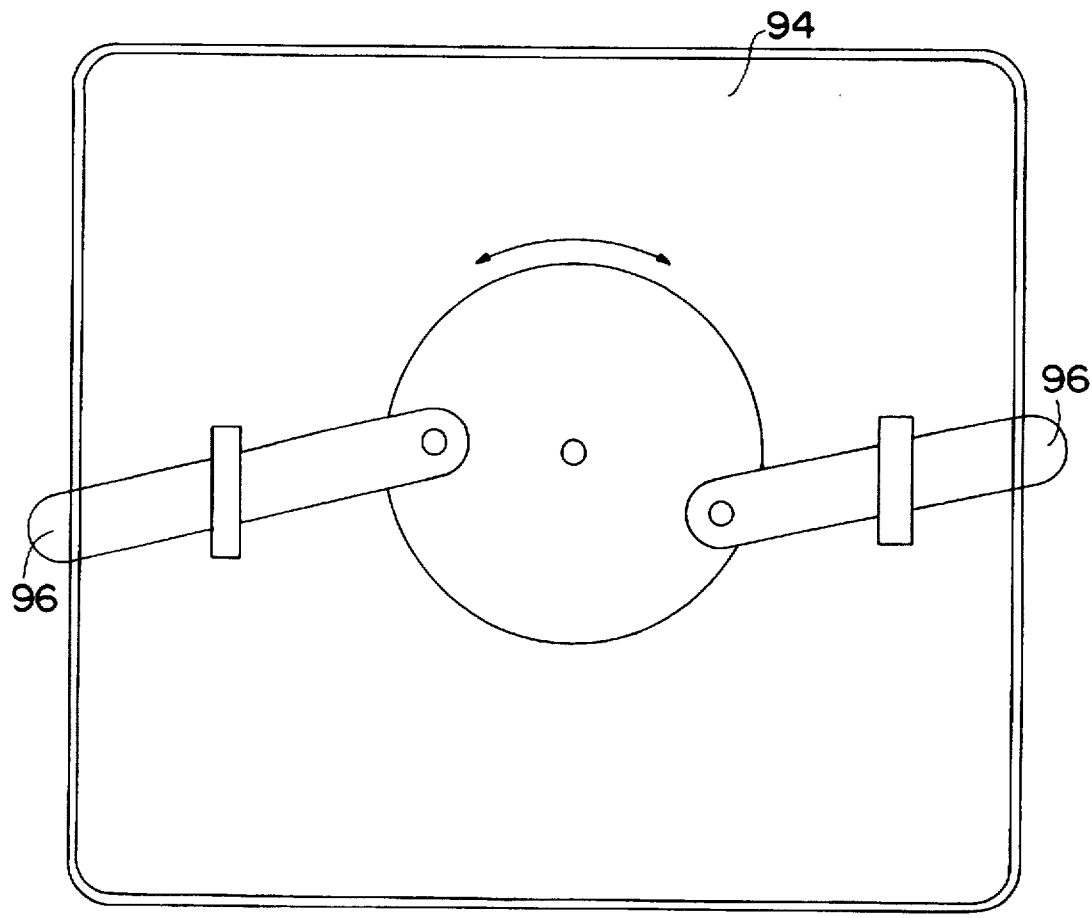
FIG. 4 is a plan view, taken from the inside of the end cover, and showing details of the locking mechanism of the end cover in accordance with a preferred embodiment of the invention.

Referring to FIGS. 2–4, the sterilization, transporting and storage tray assembly of the present invention 20 consists of a rectangularly shaped open rack 22 and a plurality of trays 24, 26, 28 slidably mounted therein on rails 30, 32, 34. Trays 24, 26, 28 each consist of a box-like tray having a tray bottom 36a, 36b, 36c, respectively, two generally perpendicular upwardly projecting sidewalls 38a, 38b, 38c, and opposed end walls 40a, 40b, 40c, respectively, terminating in rolled top edges 42a, 42b, 42c and 44a, 44b, 44c, respectively. Tray bottoms 36a, 36b, 36c include a plurality of spaced apertures (not shown), typically arranged in a predetermined pattern, for permitting ingress and egress of steam or other gaseous sterilants, and allow for condensation drainage. A plurality of resiliently deformable instrument supports may be provided, in known manner, such as shown, for example, in U.S. Pat. No. 5,599,512 assigned to Poly Vac, Incorporated, for selectively holding and cushioning surgical instruments in the tray. Alternatively, the tray bottoms may be molded to accommodate specific instruments in accordance with prior art designs.

Rack 22 comprises a generally rectangularly shaped open rack comprising top and bottom walls 50, 52, and side walls 54, 56. Top and bottom walls 50, 52 comprise a plurality of spaced apertures 58, 60 preferably aligned with the apertures in trays 24, 26, 28, for permitting ingress and egress of steam of other gaseous sterilant, and allow for condensation drainage.

A feature of the present invention and advantage over prior art sterilization, transporting and storage container tray systems is the ability to selectively access any one of the trays in the stack without displacing the other trays. In order to permit such accessibility, trays 24, 26, 28 are slidably mounted on rail assemblies 30, 32, 34 so that the trays accessible from the side of the rack. In a preferred embodiment of the invention rail assemblies 30, 32,34 are integrally formed with covers 62, 64, 66 and thus rail assemblies 30, 32, 34 serve the dual purpose of covering the tray contents and also supporting the trays, slidably mounted, within the rack. Covers 62, 64 and 66 are provided with apertures 68, 70, 72, respectively, which preferably are aligned with apertures 58, 60 in the rack top and bottoms, and thus also preferably aligned with the apertures in the trays 24, 26, 28.

Rail assemblies 30, 32, 34 are vertically adjustably mounted in the side walls of rack 22 so as to accommodate different tray height arrangements. Thus, rail assemblies 30, 32, 34 are provided with pins 78 for engaging in slots 80 formed in the sidewalls 54, 56 of rack 22. Referring in particular to FIG. 3, pivotally and rotatably mounted locking tabs 90 are provided midpoint on rail assemblies 30, 32, 34 for engaging in slots 92 formed midpoint of sidewalls 54, 56 of rack 22. Thus, in order to remove or reposition a rail assembly, tab 90 is lifted and rotated, the rail assembly is then removed or repositioned by tilting the rail assembly in the rack and the tab 90 is then snapped back in locking position. Alternatively, rail assembly 30, 32, 34 may be fixedly locked in selected vertical positions in rack 22 by means of conventional fastening means such as screws or the like.

Figure 5:
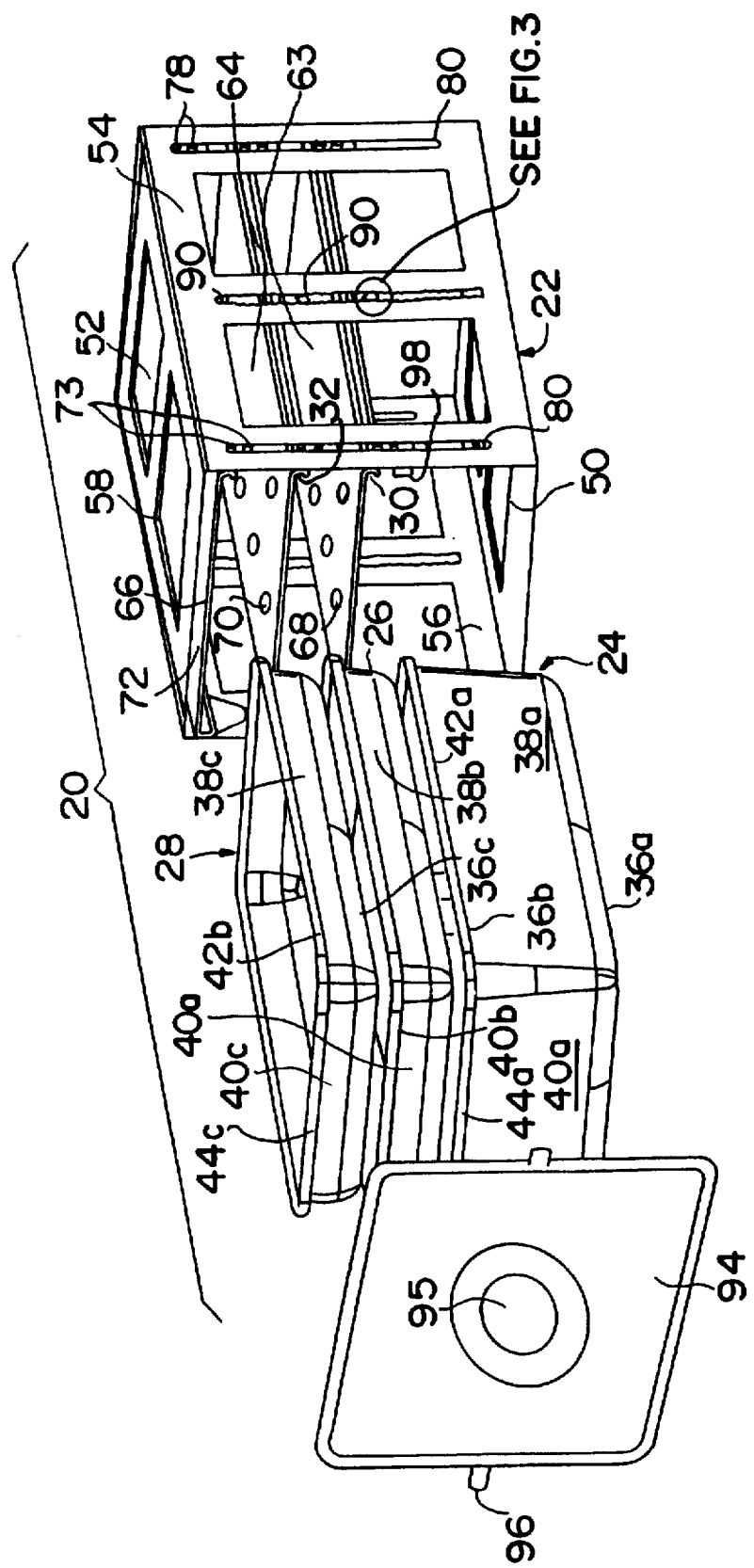
FIG. 5 is a perspective view showing details of the tray rail support elements in accordance with a preferred embodiment of the invention.
Figure 6:
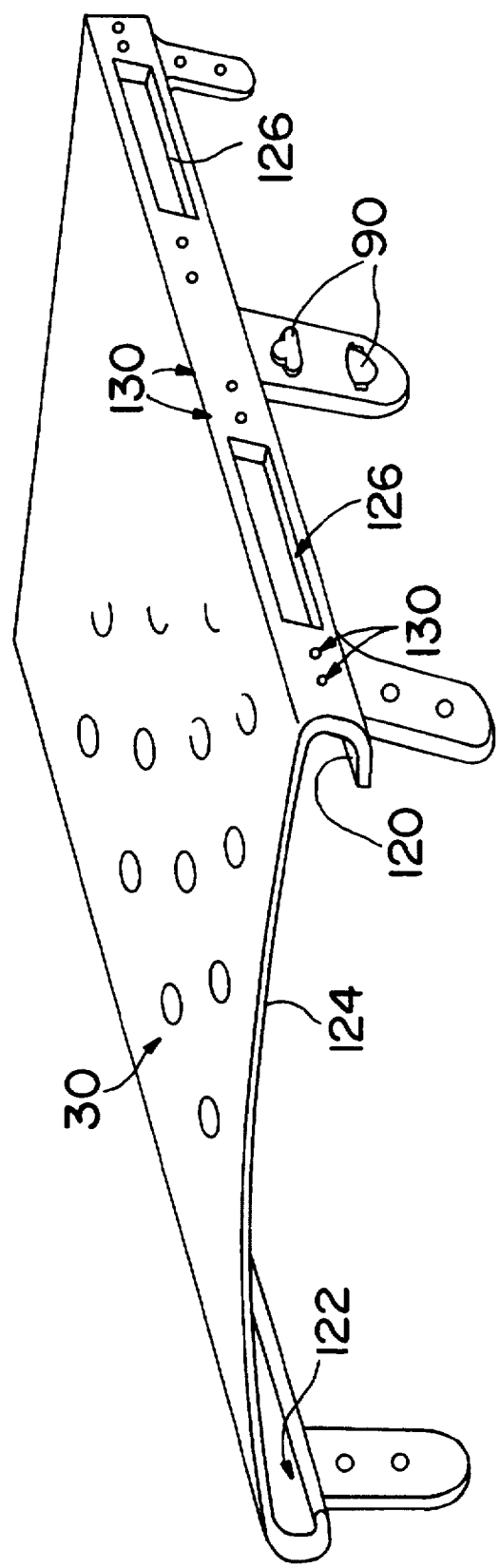
FIG. 6 is a top plan view, in partial cross section, and showing additional details of the tray rail and tray lock elements of the present invention.
Figure 7:
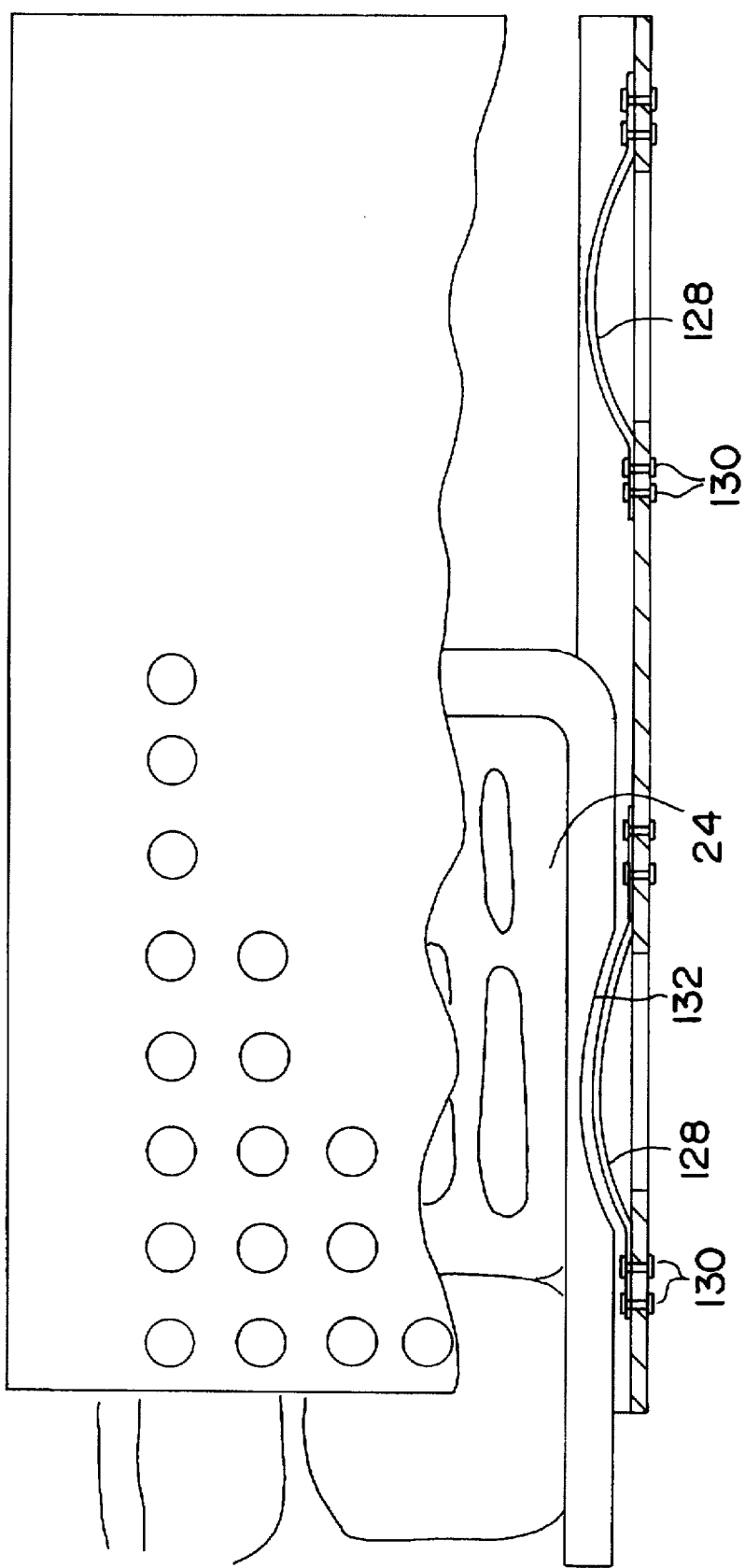
FIG. 7 shows an alternative embodiment of tray and rack system in accordance with the present invention.

FIGS. 5 and 6 illustrate one tray and rail assembly made in accordance with the present invention. For the purposes of illustration, only tray 24 and corresponding rail 30 are illustrated. However, it will be appreciated that trays 26 and 28 and rail assemblies 32 and 34 are all similarly constructed. The rail assemblies 30 are sized and shaped to slidingly engage the top edges of the trays 24 in tracks 120, 122, and preferably include a perforated web 124 which serves a dual purpose of providing a cover for the underlying trays, and for stabilizing tracks 120, 122.

A pair of windows 126 are formed in the sidewalls of tracks 120 and 122 for accommodating a spring 128 which is mechanically fixed to rails 120, 122 by rivets 130 or the like.

Formed in the sidewalls of each of the trays 24 is a contoured indent 132 for engaging with springs 128 so that the trays may be slideably releasably locked in position in the rail assemblies 30. Alternatively, the springs may be mounted on the sidewalls of the trays, for engaging detents or apertures formed in the sidewalls of the rails.

Completing the tray and rack system in accordance with the present invention are removable end caps or end walls 94 for closing the ends of rack 22. Referring also to FIG. 4, covers 94 include a rotatable handle 95 for driving rods 96 into engagement with brackets 98 provided adjacent to the edges of sidewalls 54, or through holes provided in the side walls of the rack.

The invention is susceptible to modification. For example, two "half-trays" may be slidably mounted at a selected vertical level in a rack 22. Also, as shown in FIG. 5, in order to reduce the weight of the rack member, top and bottom walls 50, 52 of the rack may be formed with large cutouts 99. Cutouts 99 may be left open or covered with a perforated lightweight material such as a plastic screening or the like.

Referring to FIGS. 8–11, yet another alternative embodiment of the invention is illustrated. In the embodiment illustrated in FIGS. 8–11, the rails 32, 34 and rail adjustments have been omitted for the ease of illustration. However, it will be understood that suitable rails which may be either fixed or adjustable will be provided in the side walls to accommodate trays.

Figure 8:
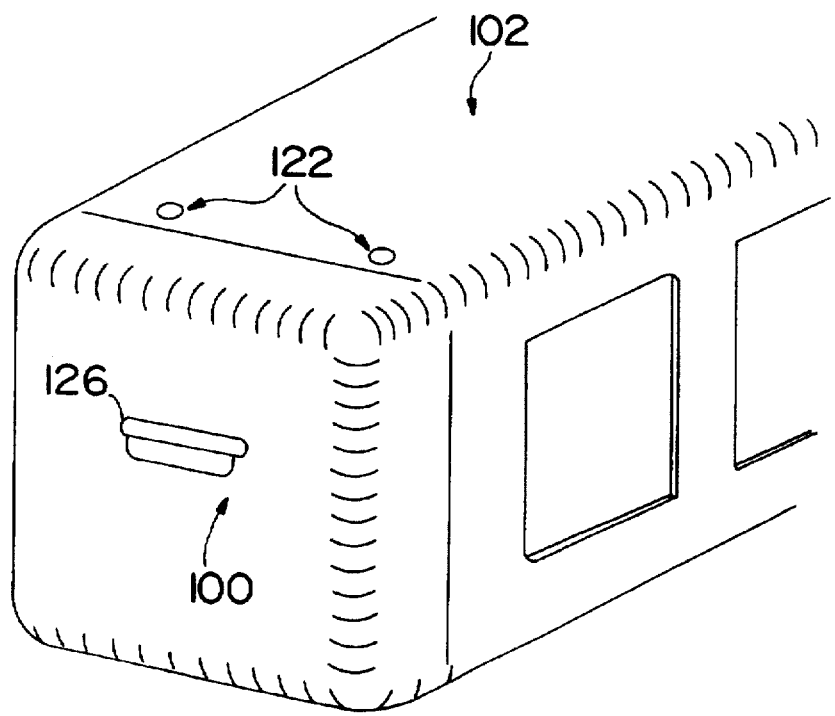
FIG. 8 shows yet another and alternative embodiment of tray and rack system made in accordance with a preferred embodiment of the present invention.
Figure 9:
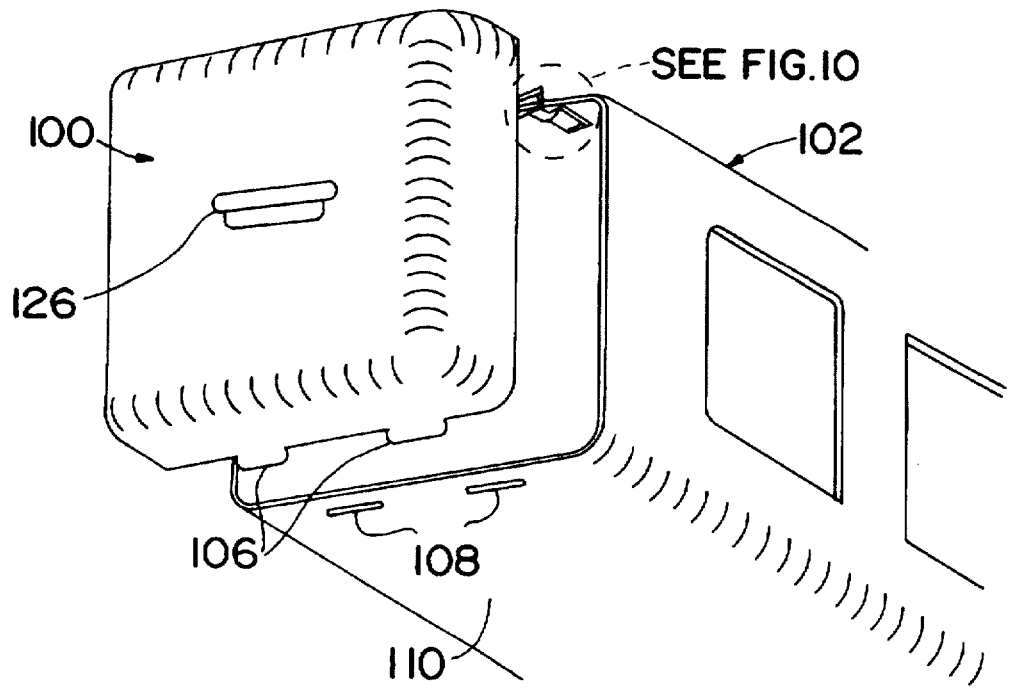
FIG. 9 is an exploded view of the FIG. 8 embodiment.
Figure 10:
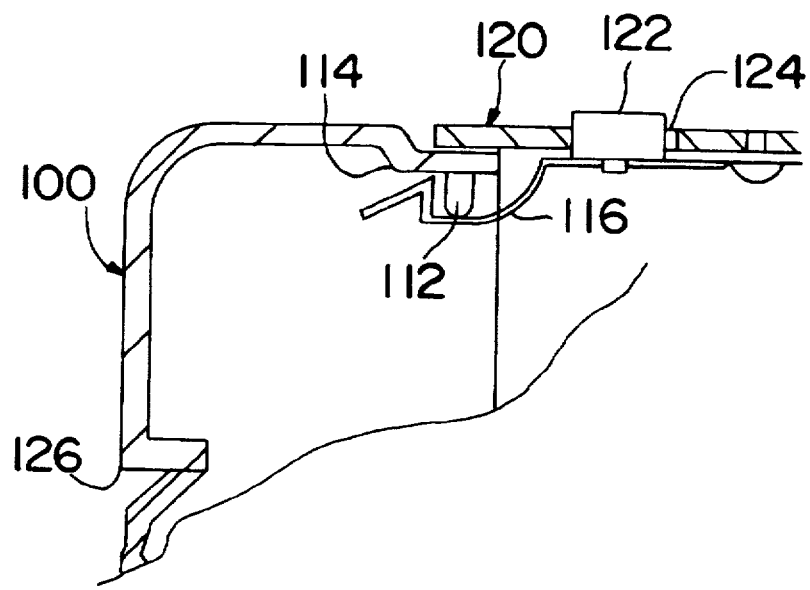
FIG. 10 is an enlarged detail view, in cross section, of the portion designated FIG. 10 in FIG. 9.
Figure 11:
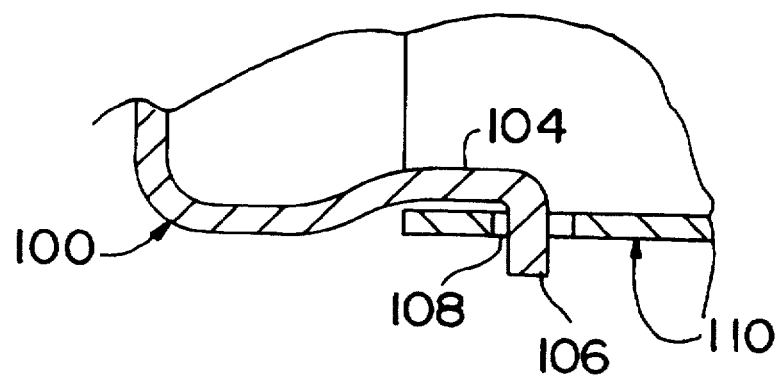
FIG. 11 is an enlarged detail view of another portion of the FIG. 8 embodiment.

Referring to FIGS. 8–11, there is shown a removable end cap 100, preferably formed of molded plastic. End cap 100 is sized and shaped to fit flush with the rack 102, and includes a peripheral inwardly disposed flange 104. Referring in particular to FIG. 9, the bottom edge of flange 104 provided with a pair of tabs 106 for engaging slots 108 formed in the bottom wall 110 of rack 102. Referring also to FIG. 8, a boss 112 is formed on the inside edge of top flange 114 for engagement by a spring tab 116 fixed to the top wall 120 of rack 102. An activation button 122 is formed through a hole 124 in top wall 120 for disengaging spring tab 116.

Completing end cap 100 is a lifting handle 126 which made the molded integrally with the panel, or affixed thereto.

A feature and advantage of the embodiment shown in FIGS. 8–11, is that sharp corners are eliminated, thus reducing the possibility that a wrap could be punctured or otherwise compromised.

Other changes are possible. For example, in order to minimize weight while providing the rigid structure, the rack may comprise a rigid frame, for example, formed of stainless steel or the like, wrapped with a outer skin of plastic or aluminum.

Still other changes may be made without departing from the spirit and scope of the invention.

We claim:

1. A stacking sterilization tray assembly for sterilizing, transporting and storing surgical instruments, and comprising a rack comprising a top wall, a bottom wall, and four side walls, at least one of said side walls being removable to provide an open side, a plurality of trays slidably mounted in said rack and removable through said open side of said rack, a plurality of spaced openings in said trays and at least the top and bottom walls of said assembly for permitting ingress and egress of sterilant therethrough for sterilizing surgical instruments placed on said trays and positioned in said rack, wherein said trays are slidably mounted on rails which are adjustably mounted in said rack, at least one of said pairs of rails including a cover member integrally formed therewith, for covering said trays when stored in said rack.

2. A sterilization tray assembly according to claim 1, and further comprising means for selectively closing the open side of said rack.

3. A sterilization tray assembly according to claim 2, wherein said means for selectively closing comprises a removable wall.

4. A sterilization tray assembly according to claim 3, and including means for selectively locking said removable wall to said rack.

5. A sterilization tray assembly according to claim 4, wherein said means for selectively locking comprises a spring tab.

6. A sterilization tray assembly according to claim 4, wherein said means for locking comprises a handle rotatably mounted on said removable wall, and arranged to drive rods into engagement with the rack.

7. A sterilization tray assembly according to claim 3, and wherein said removable wall comprises a lifting handle.

8. A sterilization tray assembly according to claim 1, and further comprising means for selectively locking said plurality of trays slideably mounted in said rack.

9. A sterilization tray assembly according to claim 1, wherein each of said trays includes a respective plurality of spaced openings which are aligned with other respective openings in top and bottom walls of said assembly.

10. A sterilization tray assembly according to claim 1, wherein said at least one cover member also includes additional respective pluralities of openings which are aligned with said other respective openings.

11. A sterilization tray assembly according to claim 1, further comprising at least one outer assembly wall cutout.

12. A stacking sterilization tray assembly for sterilizing, transporting and storing surgical instruments, and comprising a rack having at least one open side, a plurality of rails adjustably mounted in said rack, a plurality of trays slidably mounted on said rails and removable through said open side of said rack, a plurality of spaced openings in said trays and at least one outer wall of said assembly for permitting ingress and egress of sterilant therethrough for sterilizing surgical instruments placed on said trays, and positioned in said rack, and further comprising a cover member integrally formed with at least one of said pairs of rails, for covering said trays when stored in said rack.

13. A sterilization tray assembly according to claim 12, wherein said at least one cover member also includes additional respective pluralities of opening which are aligned with said other respective openings.

14. A stacking sterilization tray assembly for sterilizing, transporting and storing surgical instruments, and comprising a rack having at least one open side, a plurality of trays slidably mounted in said rack and removable through said open side of said rack, a plurality of spaced openings in said trays and at least one outer wall of said assembly for permitting ingress and egress of sterilant therethrough for sterilizing surgical instruments placed on said trays, cover members mounted in said rack for covering said trays when positioned in said rack, and means for selectively locking said plurality of trays slidably mounted in said rack, wherein said means for selectively locking comprise resiliently deformable spring members carried on said rack, and arranged to engage detents in said tray.

15. A stacking sterilization tray assembly for sterilizing, transporting and storing surgical instruments, and comprising a rack having at least one open side, a plurality of trays slidably mounted in said rack and removable through said open side of said rack, a plurality of spaced openings in said trays and at least one outer wall of said assembly for permitting ingress and egress of sterilant therethrough for sterilizing surgical instruments placed on said trays, cover members mounted in said rack for covering said trays when positioned in said rack, and means for selectively locking said plurality of trays slidably mounted in said rack, wherein said means for selectively locking comprises resiliently deformable spring members carried on said trays arranged to engage detents in said rack.

16. A sterilization tray assembly for sterilizing, transporting and storing surgical instruments, and comprising a rack having at least one open side, a plurality of trays slidably mounted in said rack and removable through said open side of said rack, and a plurality of spaced openings in said trays and at least one outer wall of said assembly for permitting ingress and egress of steriliant therethrough for sterilizing said instruments when said instruments are placed on said trays, wherein said rack comprises a plurality of perforated webs, said webs each comprising a plurality of tracks integrally formed with a respective plurality of cover members, each said web being for providing a respective cover for a respective underlying tray when said respective tray is positioned in respective tracks associated with said respective cover member, each of said cover members having a respective plurality of apertures for permitting ingress and egress of surgical instrument sterilant therethrough.

17. A sterilization tray assembly according to claim 16, wherein said tracks are adjustable.

18. A sterilization tray assembly according to claim 16, wherein windows are formed in sidewalls of said tracks for accommodating springs fixed to said rails.

* * * * *